United States Patent [19]

Block et al.

[11] 4,391,761

[45] Jul. 5, 1983

[54] PROCESS FOR THE PRODUCTION OF ARYL PHOSPHONYL COMPOUNDS

[75] Inventors: Hans-Dieter Block; Hans Dahmen, both of Cologne, Fed. Rep. of Germany

[73] Assignee: Bayer Aktiengesellschaft, Leverkusen, Fed. Rep. of Germany

[21] Appl. No.: 272,871

[22] Filed: Jun. 12, 1981

[30] Foreign Application Priority Data

Jul. 4, 1980 [DE] Fed. Rep. of Germany ....... 3025377

[51] Int. Cl.³ ............................ C07F 9/40; C07F 9/53
[52] U.S. Cl. .................................................... 260/969
[58] Field of Search ........................... 260/969; 568/14
[56] References Cited

U.S. PATENT DOCUMENTS 4,113,807  9/1978  Hechenbleikner et al. ........ 260/969

FOREIGN PATENT DOCUMENTS 1810431  6/1970  Fed. Rep. of Germany .
2442428  9/1974  Fed. Rep. of Germany .

OTHER PUBLICATIONS

Hach's Chemical Dictionary, (1961), p. 887.
The Condensed Chemical Dictionary, (1964), "V".

Primary Examiner—Anton H. Sutto
Attorney, Agent, or Firm—Sprung, Horn, Kramer & Woods

[57]  ABSTRACT

The present invention relates to a new process for the production of aryl phosphonyl compounds by the catalytic rearrangement of aryloxy phosphines in the presence of aromatic bromine compounds and zero-valent nickel.

4 Claims, No Drawings

PROCESS FOR THE PRODUCTION OF ARYL PHOSPHONYL COMPOUNDS

The present invention relates to a new process for the production of aryl phosphonyl compounds by the catalytic rearrangement of aryloxy phosphines in the presence of aromatic bromine compounds and zero-valent nickel.

The reaction according to the invention can be illustrated by the following general formula:

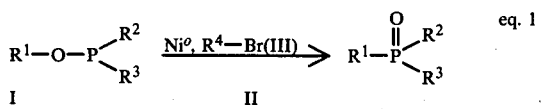

eq. 1 wherein I represents the aryloxy phosphine used as starting material and II represents the aryl phosphonyl compound obtained as the product of the reaction according to the invention and wherein the substituents given have the following meaning:

$R^1$ represents a mononuclear or polynuclear $C_6$–$C_{14}$ radical, which may be substituted by chlorine, fluorine, or by alkyl, aryl, alkoxy, aryloxy, alkenyl or cyano radicals, $R^2$ and $R^3$ represent, independently of each other, an alkyl, alkenyl or aryl radical or a radical of the structure —O—$R^5$, with $R^5$ independently of $R^1$, having the same meaning as $R^1$, $R^4$, independently of $R^1$, has the same meaning as $R^1$, and is preferably identical to $R^1$.

Thus, to explain in more detail, the process according to the invention comprises the synthesis of aryl phosphonyl acid diaryl esters from triaryl phosphites, as well as the synthesis of aryl-hydrocarbylphosphinic acid aryl esters from hydrocarbyl phosphorous acid diaryl esters and finally the synthesis of dihydrocarbyl-aryl-phosphine oxides from di-hydrocarbylphosphinous acid aryl esters, hydrocarbyl radicals to be understood as being both alkyl, alkenyl and aryl radicals.

A particularly preferred subject of the present invention is the process for producing benzene phosphonic acid diphenyl esters by the catalytic rearrangement of triphenyl phosphite in the presence of bromobenzene and zero-valent nickel.

Aryl phosphonic acid diaryl esters, aryl hydrocarbyl phosphinic acid aryl esters and dihydrocarbyl aryl phosphine oxides are known substances which can be produced by various processes. The conventional synthesis of aryl phosphonic acid diaryl esters comprises reacting aryl phosphononic acid dichlorides with phenols, the difficult synthesis of aryl phosphonic acid dichloride being a serious disadvantage of this process.

In a similar manner the hydrocarbyl aryl phosphinic acid aryl esters are able to be produced from the corresponding hydrocarbyl-aryl-phosphinic acid chlorides by reacting them with phenols; here as well the essential difficulty lies in the obtainment of the corresponding phosphinic acid chlorides.

Thus there has been no lack of attempts to modify the conventional Michaelis-Arbusow reaction, which allows the production of alkyl phosphonyl compounds from alkoxy phosphines—i.e. trialkyl phosphites, dialkyl hydrocarbyl phosphonites, alkyl dihydrocarboyl phosphinites by catalytic rearrangement, in the presence of halogen alkanes, in such a way that aryl phosphonyl compounds are able to be produced. These efforts have to a very large extent concerned benzene phosphonic acid diphenyl ester.

A number of processes which start with aryl halides and react these with phosphites, are restricted to the production of aryl phosphonic acid dialkyl ester (e.g. DE-OS No. (German Offenlegungsschrift) 1,810,431); other processes which ultimately always resort to a conventional Michaelis-Arbusow rearrangement of alkoxy phosphino groups (cf. for example 1) M. L. Honig, E. D. Weil, J.Org.Chem. 42, 379 (1977), 2) DE-OS No. 2,747,554) only give alkane phosphonic acid diaryl esters. These two processes therefore do not help to solve the present problem.

The preparative endeavours to develop a synthesis route for the production of aryl phosphonyl compounds from aryloxy phosphines have to a vary large extent concerned benzene phosphoric acid diphenyl ester and have concentrated on the catalytic rearrangement of triphenyl phosphite.

The process described in the U.S. Pat. No. 4,113,807 is for the first time successful, although it is still in many respects unsatisfactory. In order to carry out the reaction of this process triphenyl phosphite is heated with iodobenzene and a metal halide or a metal phosphite complex to temperatures above 200° C. The disadvantage of this process lies above all in the use of the expensive iodobenzene in quantities of up to 10% and in the relatively high proportion of triphenyl phosphate in the reaction product if it is desired to achieve triphenyl phosphite conversions in excess of 20%.

Distinctly better results are obtained by the process according to the invention providing rearrangement of the triphenyl phosphite carried out in the presence of the very much more readily available and inexpensive bromobenzene instead of iodobenzene, zerovalent nickel having to be present as an additional catalyst.

This result is suprising in many respects. In all known cases of reactions similar to the Michaelis-Arbusow reaction, the iodine compounds are distinctly more active than the bromine compounds, whereas the reaction according to the present invention may be carried out much more advantageously with bromobenzene than with iodobenzene.

Hitherto, there has been no shortage of attempts to replace iodobenzene by bromobenzene in reactions similar to the Michaelis-Arbusow reaction (for example J. B. Plumb, R. Obrycki, C. E. Griffin, J.Org.Chem. 31, 2455 (1966). Unfortunately, these attempts failed because it was not possible to find suitable process conditions.

With bromobenzene, the process according to the present invention is not only quicker and more complete than with iodobenzene, it is also accompanied by distinctly fewer side reactions, for example triphenyl phosphate formation. Reactions which have a certain similarity with the process according to the present invention in the form of a reaction equation, in the nature of a starting material or in the nature of the product without, however, being applicable to the reaction on which the present invention is based require either high-energy light or copper and a compound thereof as catalyst or take place under totally different conditions with almost any metal compound. By contrast, the reaction according to the present invention may only be satisfactorily carried out with zero-valent nickel as catalyst.

The process according to the invention is not limited to the conversion of triphenyl phosphite into benzene phosphonic acid diphenyl ester; on the contrary, its general applicability to many aryloxy phosphines, i.e. triaryl phosphites, phosphonous acid diaryl esters and phosphinous acid aryl esters can be considered as an essential advantage of this process.

The catalysts to be used apart from zero-valent nickel are the aryl bromides corresponding to the aryloxy group which has been or is to be rearranged.

Aryloxy phosphines of the general formula I which are suitable for the process according to the invention are, for example:
triphenyl phosphite,
tri-p-cresyl phosphite,
tri-o,m,p-cresyl phosphite,
diphenyl cresyl phosphite,
tri-p-ethylphenyl phosphite,
tri-o,m-p-ethylphenyl phosphite,
tri-o,m,p-isopropylphenyl phosphite,
diphenyl-p-isopropylphenyl phosphite, tri-isobutylphenyl phosphite,
tri-p-tert.-butylphenyl phosphite,
tri-nonylphenyl phosphite,
trioctylphenyl phosphite,
diphenyl dodecylphenyl phosphite,
tri-β-naphthyl phosphite,
tri-α-naphthyl phosphite,
tris-p-phenylphenyl phosphite,
tris-p-chlorophenyl phosphite,
tris-p-fluorophenyl phosphite,
methane phosphonous acid diphenyl ester,
ethane phosphonous acid diphenyl ester,
benzene phosphonous acid diphenyl ester,
methane phosphonous acid-di-p-cresyl ester,
methane phosphonous acid-phenyl-p-cresyl ester,
methane phosphonous acid-di-p-isopropyl phenyl ester,
methane phosphonous acid di-p-tert.-butylphenyl ester,
benzene phosphonous acid di-p-cresyl ester,
benzene phosphonous acid di-p-ethylphenyl ester,
benzene phosphonous acid di-p-isopropylphenyl ester,
benzene phosphonous acid di-p-tert.-butylphenyl ester,
dimethyl phosphinous acid phenyl ester,
diphenyl phosphinous acid phenyl ester and
diphenyl phosphinous acid cresyl ester.

The arylbromide of the general formula III required as catalyst is used in amounts of 0.2 to 10%—based on the aryloxy phosphine to be rearranged. Although higher quantities may be used they do not produce any particular advantages. In general the aryl radical $R^4$ of the aryl bromide to be used will be selected so that it corresponds with the aryl radical $R^1$ of the aryloxy group in the aryloxy phosphine to be rearranged. If, however, allowance is made for a certain amount of contamination of the product another aryl bromide can also be used. Suitable nickel (o)-containing catalysts are elemental nickel, preferably in active and in finely divided form, for example in the form of Raney nickel and also complexes of nickel (o), for example with trialkyl phosphites, triaryl phosphites, phosphonous acid esters and phosphinous acid esters, phosphines, phosphorus trifluoride, isonitriles, amines, nitrogen oxide or with carbonmonoxide and with similar ligands, in addition however those nickel compounds of higher oxidation states which are converted into zero-valent nickel under the reaction conditions, such as for example nickel oxalate, or which can be converted into zero-valent nickel. The quantities required, expressed as elemental nickel, are between 0.05 and about 10% by weight, based on the aryloxy phosphine to be rearranged.

Depending on the reaction conditions different degrees of conversion of the aryloxy phosphine concerned into the aryl phosphonyl compound can be obtained, the reaction temperature, the reaction time, the catalyst and the catalyst concentration being the most important influencing factors.

The easiest way of determining the result of the reaction is by gas chromatography. $^{31}$P-NMR-spectroscopy and the conventional oxidimetric processes for determining phosphorus (III) are also suitable as analytical methods. Mass spectrometry is a preferred technique for determining the content of aryloxy phosphine oxides, e.g. triaryl phosphate such as triphenyl phosphate.

In order to make working-up of the reaction product and isolation of the pure arylphosphonyl compound—i.e. for example the benzene phosphonic acid diphenyl ester—as easy as possible, it is of course desirable to achieve substantially complete conversion of the aryloxy phosphine with the least possible formation of aryloxy phosphine oxides.

Preferred reaction temperatures are between 250° and 350° C., more particularly between 280° and 330° C. The optimum temperature range has to be selected according to the aryloxy phosphine to be rearranged and has to be determined experimentally in each case. Triphenyl phosphite for example, is rearranged into benzene phosphonic acid diphenyl ester preferably at temperatures between 300° and 330° C. Reaction temperatures lying outside these limits generally result in incomplete reaction of the aryloxy phosphine, thus, for example, of the triphenyl phosphite, or in an increase in the secondary reactions.

In general the reaction according to the invention is carried out under an inert gas atmosphere (such as for example nitrogen or argon). The influence of oxygen may lead to partial oxidation of the aryloxy phosphine and/or nickel (o)-catalyst. Moisture should as far as possible be excluded. It is also possible to carry out the reaction according to the invention not only uder normal pressure but also under increased or reduced pressure. The use of solvents does not afford any discernible advantages. The reaction may be carried out continuously or in batches.

The reaction product may be worked up into pure arylphosphonyl compound, e.g. into pure benzene phosphonic acid diphenyl ester, by conventional measures, e.g. by removal from the non-volatile nickel catalyst by distillation or, much more effectively in terms of purity, by fractional distillation or rectification. Fractional crystallization can also be used for purification. However, purification of the product may also be carried out by wet methods, for example by washing the crude product optionally dissolved in a solvent with aqueous acids or aqueous bases or even with oxidizing solutions, optionally successively with these solutions. Measures for purifying the product with aqueous solutions may also be combined with working up by distillation.

The aryl phosphonyl compounds obtainable by the process according to the invention are able to be used as flame-proofing agents and plasticizers. Aryl phosphonic acid diaryl esters, in particular benzene phosphonic acid diphenyl esters can be used for the synthesis of polymers.

Benzene phosphonic acid diphenyl ester is an eminently suitable starting material for the production of polyphosphonates by transesterification in the melt either with bisphenols (U.S. Pat. Nos. 2,682,522 and 3,578,731, Japanese Patent Application No. 78 033 992) or with aliphatic diols (Japanese Patent Application No. 50 089 497). On account of the hitherto poor availability of benzene phosphonic acid diphenyl ester, the literature has generally described the synthesis of these polyphosphonates, which are of interest as plasticizers, flameproofing agents and as materials, from benzene phosphonic acid dichloride, which was more readily available prior to the present invention in spite of the considerable technical disadvantages involved (formation of hydrogen chloride, corrosiveness, cleavage and dissociation and rearrangement of alkyl groups and alkylene groups in the diol). The polyphosphonates which are readily obtainable from benzene phosphonic acid diphenyl ester are suitable for use as fire-retarding and plasticizing additives for virtually any thermoplastic plastic, for example polyesters (DE-OS Nos. 2,639,745 and 2,553,208), polysulphones (Japanese Patent Application No. 017 008), polyacrylonitrile (FR-PS No. 2,201,311) and viscose (Japanese Patent Application No. 40 075 821), polyphenylene oxide, polystyrene, and also for duromers, for example phenol/formaldehyde resins, and as a flame-proofing agent for cotton.

The process of the invention is illustrated by the following examples.

EXAMPLE 1

5 g of an aqueous suspension of Raney nickel are dried at 120° C./12 mm Hg for 1,0 hours. 124 g of technical grade triphenyl phosphite and 2.4 g of bromobenzene are then added. The resulting reaction mixture is heated to 320° C. with stirring for 8.5 hours under a nitrogen atmosphere.

The mixture may be distilled substantially quantitatively at 240° C./2 mm Hg.

According to its gas chromatogram, the mixture has the following composition:

| | |
|---|---|
| phenol | 5.7% |
| benzene phosphonic acid diphenyl ester | 90.6% |
| triphenyl phosphate | 2.8% |

Composition of the technical grade triphenyl phosphite determined by gas chromatography:

| | |
|---|---|
| phenol | 3.2% |
| triphenyl phosphite | 93.3% |
| triphenyl phosphate | 2.4%. |

EXAMPLE 2

50 g of an aqueous suspension of Raney nickel are dried at 130° C./12 mm Hg for 1.3 hours, particular care being taken that the drops of condensed water are removed from all parts of the glass vessel. 1240 g triphenyl phosphite and 12 g bromobenzene are then added and the entire mixture is heated with stirring to 320° C. Refluxing, which occurs at first decreases with time. After 1 hour a further 24 g bromobenzene are dropped into the reaction mixture in the course of 3 hours.

After a total of 4 hours reaction time the mixture has, according to gas chromatography, the following composition:

| | |
|---|---|
| bromobenzene | 0.6% |
| phenol | 4.0% |
| triphenyl phosphate | 0.3% |
| benzene phosphonic acid diphenyl ester | 94.0%. |

EXAMPLE 3

If the procedure according to example 2 is repeated at 310°–320° C. and at the same time analyzed at hourly intervals, in the course of 4 hours the content of benzene phosphonic acid diphenyl ester increases to 65.1% after 1 hour, to 81.2%, then to 91.7% and finally to 93.1%, whereas the triphenyl phosphite content falls from 26.8% to 11.5%, to 0.5% and finally to an undetectable amount. The contents of phenol and triphenyl phosphate remain constantly at 4,6–5,0% and 0.5–0.7% respectively, the quantity of these being mainly due to the impurities in the starting materials and also the residual water content in the Raney nickel. A part of the bromine introduced with the bromobenzene leaves the reaction mixture again in the form of hydrogen bromide.

EXAMPLE 4

250 g of an aqueous suspension of Raney nickel are dried carefully at 130° C./12 mm Hg for 1.5 hours. Then 6200 g triphenyl phosphite and 60 g bromobenzene are added, the mixture is heated with stirring to 310° C. and after reaching this temperature a further 120 g of bromobenzene are added in the course of 2 hours. After a total of 4 hours the reaction mixture is distilled from the reaction vessel. In the course of a rough preseparation process the destillate which is passed over at up to a top temperature of 240° C. under a pressure of about 2–5 mm Hg is taken off as forerun and the portion passed over thereafter is obtained as the product in an amount of 5810 g. Its composition determined by gas chromatography is:

| | |
|---|---|
| bromobenzene | 0.05% |
| phenol | 0.25% |
| triphenyl phosphite | 0.5% |
| benzene phosphonic acid diphenyl ester | 96.5% |
| triphenyl phosphate | 0.6% |

A part of this product is rectified in a conventional manner over a short packed column at a reflux ratio of 2:1. The main running is 99.3% strength benzene phosphonic acid diphenyl ester.

EXAMPLE 5

A reaction mixture obtained according to example 3 by an approximately one hour long reaction of technical grade triphenyl phosphite with bromobenzene and Raney nickel is distilled over in vacuo. The distillate which contains 40.4% triphenyl phosphite, 6.2% triphenyl phosphate, 50.7% benzene phosphonic acid diphenyl ester and 1.2% phenol, is left to stand at room temperature. From the matted slurry of crystals which forms the non-crystallized liquid part is poured off after 2 days and the slurry of crystals is left to drain. The resulted slurry of crystals contains 83.0% of benzene phosphonic acid diphenyl ester. Further fractional crystallization gives a more purified product.

COMPARISON EXAMPLE A 5 g of an aqueous suspension of Raney nickel are dried at 120° C./12 mm Hg. 124 of triphenyl phosphite and 2.4 g of iodobenzene are then added. The resulting reaction mixture is heated to 320° C. with stirring for 4 hours under a nitrogen atmosphere.

The mixture may be distilled substantially quantitatively at 240° C./2 mm Hg.

According to its gas chromatogram, the distillate has the following composition;

| phenol | 6.2% |
|---|---|
| benzene phosphonic acid diphenyl ester | 47.5% |
| triphenyl phosphate | 22.8% |
| triphenyl phosphite | 18.8% |

COMPARISON EXAMPLE B 5 g of an aqueous suspension of Raney nickel are dried at 120° C./12 mm Hg. 124 g of triphenyl phosphite and 2.4 g of chlorobenzene are then added. The resulting reaction mixture is heated to 320° C. with stirring for 8 hours under a nitrogen atmosphere.

The mixture may be distilled substantially quantitatively at 240° C./2 mm Hg.

According to its gas chromatogram, the distillate has the following composition:

| phenol | 2.9% |
|---|---|
| benzene phosphonic acid diphenyl ester | 12.3% |
| triphenyl phosphate | 10.1% |
| triphenyl phosphite | 72.2%. |

COMPARISON EXAMPLE C 5 g of an aqueous suspension of Raney cobalt are dried at 120° C./12 mm Hg. 124 g of triphenyl phosphite and 2.4 g of bromobenzene are then added and the resulting stirred mixture is heated to 320° C. for 4 hours under a nitrogen atmosphere. Thereafter, the mixture has the following composition:

| phenol | 4.7% |
|---|---|
| benzene phosphonic acid diphenyl ester | 10.4% |
| triphenyl phosphite | 72.4% |
| triphenyl phosphate | 9.3%. |

COMPARISON EXAMPLE D

A mixture of 124 g of triphenyl phosphite, 2.4 g of bromobenzene and 3 g of anhydrous nickel-(II)-chloride is heated to 320° C. for 8.5 hours. The reaction mixture is then distilled.

The distillate has the following composition:

| phenol | 3.6% |
|---|---|
| benzene phosphonic acid diphenyl ester | 38.2% |
| triphenyl phosphite | 44.7% |
| triphenyl phosphate | 11.4% |

An even lower degree of conversion is obtained using nickel bromide instead of nickel chloride.

COMPARISON EXAMPLE E

Comparison example D is modified to the extent that 2.4 g of iodobenzene are used instead of bromobenzene. In this case, the distillate has the following composition:

| phenol | 3.2% |
|---|---|
| benzene phosphonic acid diphenyl ester | 7.0% |
| triphenyl phosphite | 74.1% |
| triphenyl phosphate | 14.8%. |

COMPARISON EXAMPLE F

If, in comparison example D, the nickel chloride is replaced by copper-(I)-chloride or copper-(II)-chloride, benzene phosphonic acid diphenyl ester contents of only 1.1% and 2.5%, respectively, are obtained in the reaction mixture, given the same reaction temperature and time.

EXAMPLE 6

120 g triphenyl phosphite, 4 g bromobenzene and 2 ml nickel tetracarbonyl are mixed, heated to 320° C. and kept at this temperature for 4 hours. According to its gas chromatogram the reaction mixture then contains

| benzene phosphonic acid diphenyl ester, | 92.2% |
|---|---|
| triphenyl phosphate | 0.3% |
| triphenyl phosphite | 0.6%. |

EXAMPLE 7

30 ml of a solution of 15.5 mmol nickel tetrakis(-triphenyl phosphite) in triphenyl phosphite are added to 124 g of triphenylphosphite and 5 g bromobenzene and heated to 320° C. for 4 hours. Then, according to gas chromatographic analysis the reaction mixture contains 93.3% of benzene phosphonic acid diphenyl ester.

EXAMPLE 8

141 g tri-p-cresyl phosphite, 2.5 ml nickel tetracarbonyl and 5 g p-bromotoluene are mixed, heated to 320° C. and kept at this temperature for 1 hour. Then the reaction mixture contains

| p-methylbenzene phosphonic acid di-p-cresyl ester | 93.5% |
|---|---|
| tricresyl phosphite | 1.4% |
| cresol | 4.5%. |

EXAMPLE 9

141 g tri-p-cresyl phosphite, 2.5 ml nickel tetracarbonyl and 4 g bromobenzene are heated together to 320° C. and kept at this temperature for 4 hours. Then the reaction mixture contains

| | |
|---|---|
| p-methylbenzene phosphonic acid di-p-cresyl ester | 79.3% |
| benzene phosphonic acid di-p-cresyl ester | 5.1%. |

EXAMPLE 10

191 g tris-p-tert.-butyl phenyl phosphite, 2 ml nickel tetracarbonyl and 4 g bromobenzene are introduced together into the reaction vessel and are heated slowly. Upon termination of the carbon monoxide evolution the reaction mixture is heated to 320° C. and kept at this temperature for 4 hours. According to the gas chromatogram 2.3% p-tert.-butylphenyl and 5.6% tris-p-tert.-butylphenyl phosphite are obtained besides 90.7% p-tert.-butyl benzene phosphonic acid-di-p-tert.-butyl phenyl ester.

EXAMPLE 11

5 g of an aqueous suspension of Raney nickel are dried for 1 hour at 120° C./12 mm Hg. Then 165 g tris-p-chlorophenyl phosphite and 2.4 g bromobenzene are added and this mixture is heated with stirring to 320° C. After 4 hours 2.9% of tris-p-chlorophenyl phosphite are still present in the mixture according to gas chromatographic analysis.

Benzene phosphonic acid di-p-chlorophenyl ester and p-chlorobenzene phosphonic acid di-p-chlorophenyl ester, as products, form 5.4% and 74.1%, respectively, of the mixture.

We claim:

1. Process for the production of aryl phosphonyl compounds of the general formula

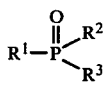   I wherein
   $R^1$ represents a mono- or polynuclear $C_6$-$C_{14}$ aryl radical, which can be substituted by chlorine, fluorine or by alkyl, aryl, alkoxy, aryloxy, alkenyl or cyano radicals,
   $R^2$ and $R^3$, independently of each other represent an alkyl, alkenyl or aryl radical or a radical of the structure O-$R^5$, in which $R^5$, independently of $R^1$, has the same meaning as $R^1$,
by the catalytic rearrangement of aryloxy phosphines of the general formula II

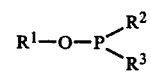   II wherein
   $R^1$, $R^2$ and $R^3$ have the meanining indicated above, characterized in that the rearrangement is carried out in the presence of aromatic bromine compounds and a zero-valent nickel catalyst selected from the group consisting of elemental nickel, a complex of nickel (o) with a trialkyl phosphite, a triaryl phosphite, a phosphonous acid ester, a phosphinous acid ester, a phosphine, phosphorus trifluoride, an isonitrile, an amine, a nitrogen oxide, carbon monoxide, and a compound of nickel in an oxidation state higher than zero wherein the nickel is converted to zero-valent nickel under the reaction conditions.

2. Process according to claim 1, characterized in that the aromatic bromine compound used has the general formula:

in which
   $R^1$ has the meaning given above.

3. Process according to claim 1 or 2, characterized in that
   $R^2$ and $R^3$ are identical with —O—$R^1$.

4. Process according to claim 1 or 2, characterized in that triphenyl phosphite is rearranged into benzene phosphonic acid diphenyl ester.

* * * * *